US009782292B2

(12) United States Patent
Hufford et al.

(10) Patent No.: US 9,782,292 B2
(45) Date of Patent: Oct. 10, 2017

(54) GUIDE TOOL FOR CATHETER INSERTION

(71) Applicant: The Charles Stark Draper Laboratory, Inc., Cambridge, MA (US)

(72) Inventors: Kevin Hufford, St. Petersburg, FL (US); Christopher V. Trainor, Boxborough, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 241 days.

(21) Appl. No.: 14/563,230

(22) Filed: Dec. 8, 2014

(65) Prior Publication Data
US 2015/0157497 A1 Jun. 11, 2015

Related U.S. Application Data

(60) Provisional application No. 61/912,751, filed on Dec. 6, 2013.

(51) Int. Cl.
*A61B 19/00* (2006.01)
*G06F 19/00* (2011.01)
*A61F 9/007* (2006.01)
*A61M 25/01* (2006.01)
*A61B 34/00* (2016.01)
*A61B 90/50* (2016.01)
(Continued)

(52) U.S. Cl.
CPC .............. *A61F 9/007* (2013.01); *A61B 34/70* (2016.02); *A61B 34/77* (2016.02); *A61B 90/11* (2016.02); *A61B 90/50* (2016.02); *A61M 25/01* (2013.01); *A61B 2090/064* (2016.02)

(58) Field of Classification Search
USPC .......................................... 606/130; 700/245
See application file for complete search history.

(56) References Cited

U.S. PATENT DOCUMENTS 5,410,638 A 4/1995 Colgate et al.
5,626,595 A 5/1997 Sklar et al.
(Continued)

FOREIGN PATENT DOCUMENTS

JP 2009-273829 A 11/2009

OTHER PUBLICATIONS

International Search Report and Written Opinion dated Apr. 17, 2015 in PCT Application No. PCT/US2014/069069.
(Continued)

*Primary Examiner* — Nicole F Johnson
*Assistant Examiner* — Nicole F. Lavert
(74) *Attorney, Agent, or Firm* — Foley & Lardner LLP; Paul S. Hunter

(57) ABSTRACT

The present disclosure describes a catheter guide tool. More particularly, the catheter guide tool is a bi-stable device used for the insertion and advancement of a catheter. The catheter guide tool includes a gimbal. A guide axis runs through the gimbal. A catheter advancement mechanism is coupled to the gimbal and configured to advance the catheter along the guide axis. The guide tool also includes a pivot assembly coupling the gimbal to a support platform. The pivot assembly is configured to pivot the guide axis from a first position perpendicular to a target surface to a second position tangential to the target surface along a single primary plane of rotation of the gimbal.

18 Claims, 5 Drawing Sheets

(51) Int. Cl.
A61B 90/11 (2016.01)
A61B 90/00 (2016.01)

(56) References Cited

U.S. PATENT DOCUMENTS

| | | |
|---|---|---|
| 5,808,665 A | 9/1998 | Green |
| 6,936,053 B1 | 8/2005 | Weiss |
| 7,217,263 B2 | 5/2007 | Humayun et al. |
| 7,890,211 B2 | 2/2011 | Green |
| 2003/0057347 A1 | 3/2003 | Weiss |
| 2004/0024387 A1 | 2/2004 | Payandeh et al. |
| 2005/0234435 A1 | 10/2005 | Layer |
| 2008/0091066 A1 | 4/2008 | Sholev |
| 2008/0167750 A1* | 7/2008 | Stahler .................. A61B 34/37 700/245 |
| 2009/0161827 A1 | 6/2009 | Gertner et al. |
| 2009/0207239 A1* | 8/2009 | Warmerdam ........ H02K 41/031 348/61 |
| 2010/0301179 A1* | 12/2010 | Brown ................ B25H 1/0021 248/124.1 |
| 2013/0165854 A1 | 6/2013 | Sandhu et al. |

OTHER PUBLICATIONS

International Preliminary Report on Patentability for International Application No. PCT/US2014/069069 dated Jun. 16, 2016.

* cited by examiner

GUIDE TOOL FOR CATHETER INSERTION

RELATED PATENT APPLICATIONS

This application claims priority to Provisional U.S. Patent Application No. 61/912,751, filed Dec. 6, 2013 and titled "GUIDE TOOL FOR CATHETER INSERTION," which is incorporated herein by reference in its entirety.

BACKGROUND OF THE DISCLOSURE

During some medical procedures catheters are inserted into anatomical structures. For example, during some ophthalmic procedures a catheter is inserted into the posterior of the eye. Insertion and advancement of the catheter into the anatomical structure can cause complications such as perforations of surrounding tissue.

SUMMARY OF THE DISCLOSURE

According to one aspect of the disclosure, a catheter guide tool includes a gimbal. A guide axis runs through the gimbal. A catheter advancement mechanism is coupled to the gimbal and configured to advance a catheter along the guide axis. The guide tool also includes a pivot assembly coupling the gimbal to a support platform. The pivot assembly is configured to pivot the guide axis from a first position perpendicular to a target surface to a second position tangential to the target surface substantially along a single primary plane of rotation of the gimbal.

In some implementations, the pivot assembly includes a first two-bar linkage and a second two-bar linkage. The second two-bar linkage is coupled to the gimbal by a first rotational joint and to the support platform by a second rotational joint. The pivot assembly is bi-stable between the first position and the second position. In some implementations, the gimbal further includes at least one interior gimbal.

In some implementations, the catheter advancement mechanism is configured to scale an output movement to between about $\frac{1}{10}$ and about $\frac{1}{10000}$ of an input movement. In some implementations, the catheter advancement mechanism has a movement resolution between about 0.1 µm and about 100 µm. The guide tool also includes an actuator to drive the pivot assembly from the first position to the second position. The catheter advancement mechanism includes least one force sensor in some implementations. In some implementations, the support platform includes an articulating arm and the pivot assembly includes a damper to provide limited movement to within about 0.001° and about 10° of the primary plane of rotation.

According to another aspect of the disclosure, a method for inserting a catheter includes providing a catheter guide tool. The guide tool includes a gimbal with a guide axis. The guide tool also include a catheter advancement mechanism coupled to the gimbal and configured to advance a catheter along the guide axis. The guide tool also includes a linkage coupling the gimbal to a support platform and configured to pivot the guide axis from a first position perpendicular to a target surface to a second position tangential to the target surface substantially along a single primary plane of rotation of the gimbal. The method also includes advancing a catheter tip into an incision made into tissue, an organ, or an organ system, and pivoting the gimbal to the second position about the catheter tip. The catheter tip is then advanced toward an anatomical target within or beneath the tissue, the organ, or organ system.

In some implementations, the incision is made in a sclera of the eye and includes advancing the tip of the catheter toward the posterior of the eye. In some implementations of the method, a fluid is injected through the catheter tip.

In some implementations, the linkage is bi-stable between the first position and the second position. In some implementations, the method also includes scaling an output movement by the catheter guide tool to between about $\frac{1}{10}$ and about $\frac{1}{10000}$ of an input movement to the catheter guide tool.

In some implementations, the method includes pivoting the gimbal to the second position with a actuator and damping the pivot to the second position with a damper.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The disclosure describes systems and methods related to a catheter guide tool. The guide tool is a bi-stable device that enables controlled insertion of a catheter. In a bi-stable configuration, the guide tool is configured to maintain the catheter at a first position during a first part of the procedure and then pivot the catheter to a second position during a second part of the procedure. The guide tool described herein can be used in ophthalmic procedures, microvascular procedures, neurosurgery procedures, plastic surgery procedures, pediatric surgery procedures, and perinatal procedural interventions. The catheter may be used for therapeutic delivery, site sampling of liquid or tissue, biopsy, or aspiration.

Figure 1:
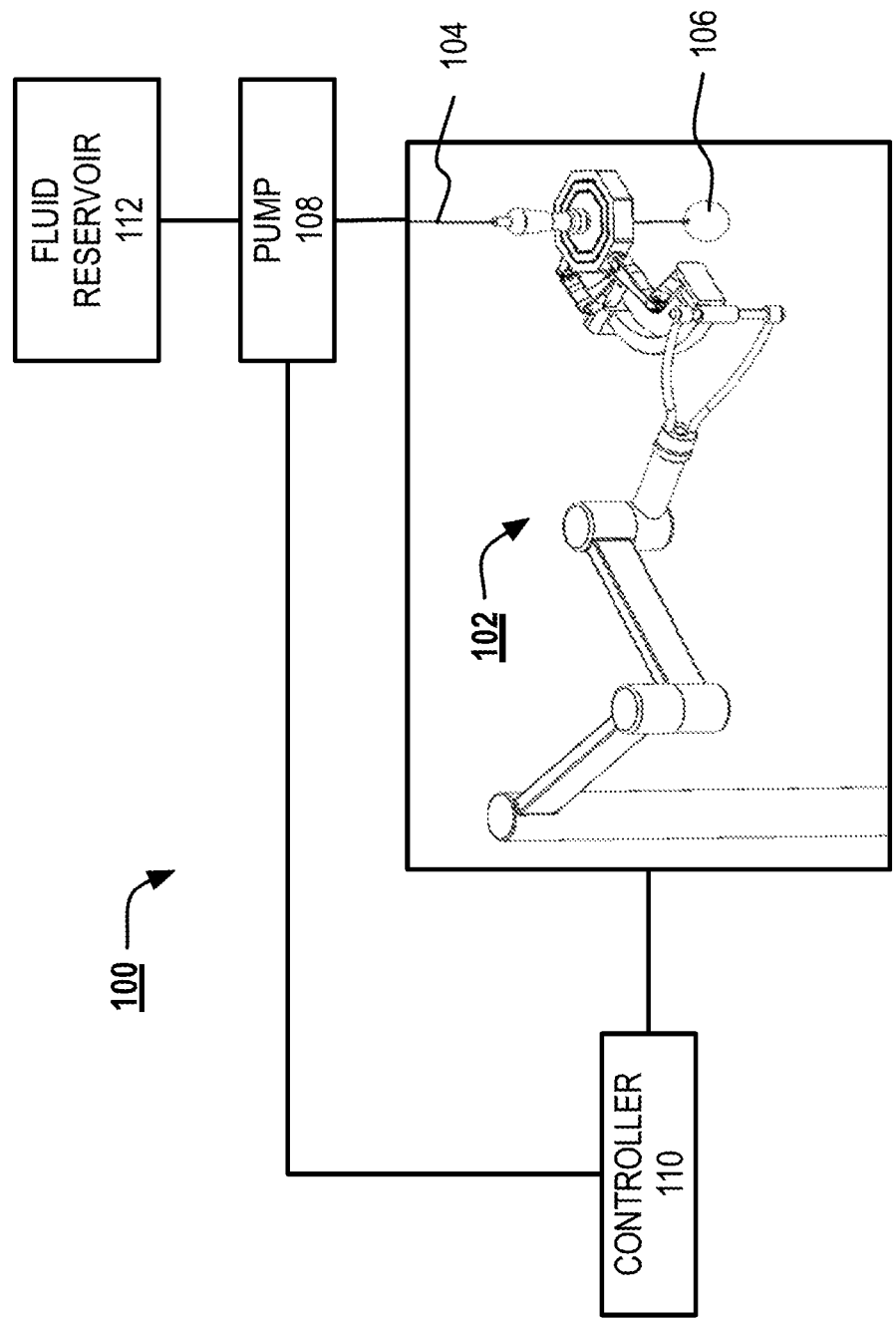
FIG. 1 illustrates an example system for inserting a catheter into an anatomical structure.

FIG. 1 illustrates a system 100 for inserting a catheter into an anatomical structure, such as the eye of a patient. The system 100 includes a catheter guide tool 102 that is used to insert a catheter 104 into an eye 106 (or other anatomical structure). The guide tool 102 is a bi-stable device used to position and advance the catheter 104 toward the target within the anatomical structure. The system 100 also includes a pump 108 that is controlled by a controller 110. The controller 110 actuates the pump 108 to flow a fluid into and out of the catheter 104. The system 100 also includes a fluid reservoir 112 from which the pump 108 draws fluid. The controller 110 is also coupled to the guide tool 102 and in some implementations controls the movement of the guide tool and the advancement of the catheter 104.

The system 100 includes a pump 108 to flow or retract a fluid through the catheter 104. The pump 108 can be any medical grade pump. In some implementations, the pump 108 is configured to generate a plurality of flow profiles, as controlled by the controller 110. In some implementations, the flow profile includes, but is not limited to, flow rate, flow direction, total volume injected (or withdrawn), flow duration, and flow waveform (e.g., square wave or sinusoidal wave). In some implementations, the pump 108 is a syringe coupled to a bi-directional syringe pump. The bi-directional syringe pump is controlled by the controller 110 to inject and withdraw fluids. The syringe pump includes a motor-driven linear actuator that uses a helical/screw drive to convert the rotation of the motor into a linear displacement. The linear displacement depresses the plunger of a syringe and causes liquid to be dispensed. In some implementations, the pump 108 is controlled by a push button, a foot pedal, voice command, or other user input.

In other implementations, the pump 108 is a peristaltic pump coupled to the catheter 104. The peristaltic pump includes a drive motor coupled to a pump head. As the motor rotates, the multiple rollers on the pump head impinge upon a flexible segment of tubing and at least partially occlude the tubing. The occlusion causes a localized increase in pressure that moves a fixed bolus of fluid through the tubing. Reversing the direction of the motor reverses the flow of liquid, and causes a withdrawal of fluid from the catheter 104. In other implementations, the pump 108 is a piezoelectrically-driven membrane at the proximal end of the catheter 104.

The system 100 also includes a controller 110 that controls the pump 108 and the guide tool 102. In some implementations, the controller 110 is a general purpose computing device. For example, the controller 110 can be a desktop computer, a laptop, tablet computer, or smartphone. In other implementations, the controller 110 is a special purpose computer device and includes one or more processors and at least one computer readable medium, such as a hard drive, compact discs, or other storage device. Processor executable instructions are stored on the computer readable medium. When executed, the instructions cause the controller 110 to perform the functions and methods described herein. For example, the guide tool 102 can be bi-stable and include two positions. The controller 110 can control actuators that move the guide tool 102 between the two bi-stable positions of the guide tool 102. The controller 110 can also control the pump 108 to flow liquid from the fluid reservoir 112 into the catheter 104 at a predetermined rate. The controller 110 can also control the advancement of the catheter 104. For example, a medical professional depress a button, which causes the controller 110 to initiate a motor that drives the catheter 104.

The system 100 also includes a catheter 104. The catheter 104 can be any medical grade catheter. In some implementations, the catheter 104 in is any type of conduit or channel such as, but not limited to, a cannula, needle, a microcannula, a microbore, a tube, or endoscope. The diameter of the catheter 104 is between about 100 μm and about 2 mm, between about 100 μm and about 250 μm, between about 250 μm and about 1 mm, between about 250 μm and about 500 μm, between about 250 μm and about 400 μm, or between about 250 μm and about 350 μm. The catheter 104 includes at least one internal lumen. In some implementations, the catheter 104 includes a plurality of lumens. For example, the catheter 104 can include a first lumen for the delivery of a dilatory liquid and a second lumen for the delivery of a therapeutic agent.

In some implementations, the catheter 104 includes depth markings along the length of the catheter 104. In some implementations, detecting the arrival of the catheter 104 at the target location is achieved by a user's visual observation of a given depth marking on the catheter 104. The depth marking indicates the correct insertion depth has been achieved. In other implementations, the tip of the catheter 104 is tracked with optical tracking by an operative-field camera or fundoscope that detects and tracks the motion of insertion depth-markings on the catheter or an optical encoder mounted near or on the catheter.

In some implementations, the body of the catheter 104 includes a fiber optic cable or the wall of the catheter 104 is configured to transmit light along the length of the catheter 104. In some implementations, the catheter 104 includes a radio opaque material that enables the catheter 104 to be visualized in a radiograph. In some implementations, the catheter 104 includes sensors, such as, but not limited to, temperature, pressure, flow sensors, spectrometers, or any combination thereof. The sensors can be configured to measure tissue density or optical properties of an eye or other anatomical structure. The sensors can be used to determine site suitability for catheter insertion. In some implementations the catheter 104 includes one or more sensors, and the controller 110 receives data from the sensors to set flow parameters, such as, but not limited to: flow rate, flow direction, flow profile, pressure, or a combination thereof, responsive to the data received from the sensors.

The system 100 also includes a guide tool 102. The guide tool 102 is described further in relation to FIGS. 2-4. The guide tool 102 is configured to position and advance the catheter 104 during a catheter insertion procedure. As an overview, the guide tool 102 includes a gimbal that includes a guide axis. The catheter 104 is advanced and retracted along the guide axis by a catheter advancement mechanism of the guide tool 102. A pivot assembly couples the gimbal to a support platform. The pivot assembly enables the gimbal to pivot the guide axis from a first position to a second position substantially along a single primary plane of rotation. In some implementations, the guide tool 102 is bi-stable between the first and the second position. In a bi-stable configuration, the guide tool 102 only stops and maintains its set guide axis position when in one of the two bi-stable positions. For example, if the medical professional positioned the guide tool 102 such that the guide axis 218 was on the single primary plane of rotation, but not at one of the two bi-stable positions, the guide tool 102 would automatically move to one of the bi-stable positions. In some implementations, the guide tool 102 provides feedback (e.g., haptic feedback) to the medical professional to assist the medical professional in moving between the two bi-stable positions. For example, the medical professional may be able to move the guide tool 102 freely between the two bi-stable positions; however, the haptic feedback may provide a "virtual surface" that limits the movement of the guide tool 102 from moving substantially past the two bi-stable positions. For example, the guide tool 102 may provide haptic feedback as the guide tool 102 nears one of the two bi-stable positions. Upon reaching one of the bi-stable positions, the haptic feedback may prevent the medical professional from moving the guide tool 102 substantially beyond the reached bi-stable position.

Figure 2:
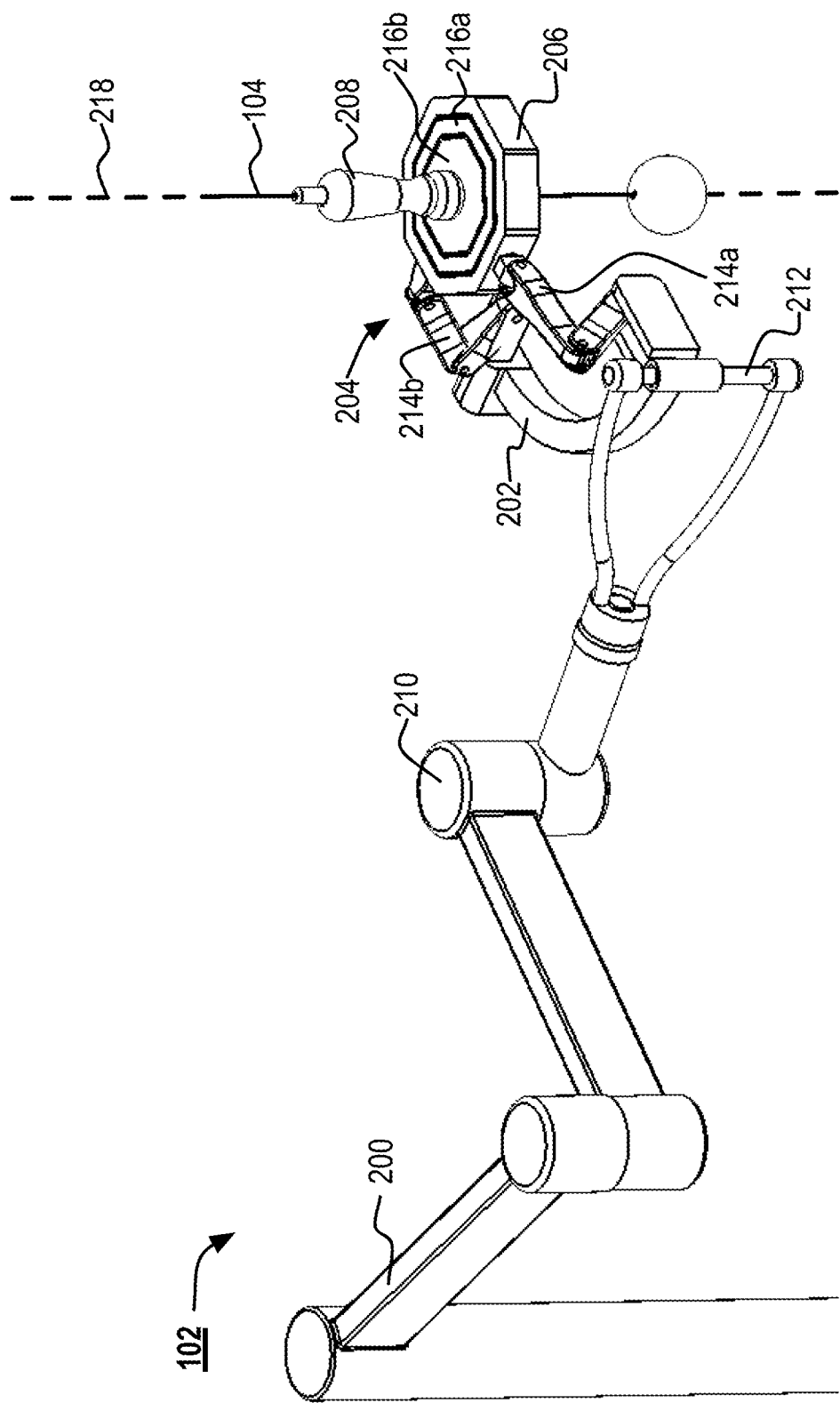
FIG. 2 illustrates the example guide tool of FIG. 1 in greater detail.

FIG. 2 illustrates the example guide tool 102 of FIG. 1 in greater detail. The guide tool 102 includes a support arm 200 (which may also be referred to as an articulating arm 200). The support arm 200 is coupled to a support platform 202. A pivot assembly 204 couples the support platform 202 to a gimbal 206. A handle 208 is coupled to the gimbal 206 and includes a catheter advancement mechanism.

The guide tool 102 includes a support arm 200. The support arm 200 provides support for the support platform 202 and is configured such that a medical provider may position the catheter 104 above the eye (or other anatomical structure) of the patient. The support arm 200 includes a number of joints 210 that provide the support arm 200 degrees of freedom to enable the positioning of the catheter 104 above the patient's eye. In some implementations, the support arm 200 is configured to include an appropriate number of degrees of freedom to position the gimbal 206 above the patient's eye. In some implementations, the support arm 200 includes a vertical rod 212 to which the support platform 202 is coupled. Fine adjustments in the vertical position of the gimbal 206 can be made by sliding the support platform 202 vertically along the vertical rod 212.

The guide tool 102 also includes a support platform 202 that is coupled to the support arm 200. The support platform 202 provides a support to which the pivot assembly 204 is coupled. In some implementations, the support platform 202 rests on the patient's orbit (or face) and enables the catheter 104 to be registered to the patient's eye. Resting the support platform 202 on the patient's face can also enable the guide tool 102 to track patient motion and reduce the likelihood of motion-related complications. For example, the catheter 104 can move in unison with the patient as the patient moves. The synchronized movement of the support platform 202 and the catheter 104 can reduce the chances of the patient moving without the catheter moving in unison, which can cause the catheter 104 to perforate the eye. In some implementations, the support platform 202 includes force sensors, which can enable the support platform 202 and the support arm 200 to move automatically in response to a patient's motion. As illustrated the support platform 202 is a quarter-circle bar. In other implementations, the support platform 202 can be a closed-loop or a half-circle support bar. In some implementations, the support platform 202 is manufactured from, or includes, a medical grade metal, such as stainless steel, aluminum, or titanium. In these implementations, the support platform 202 can withstand sterilization and may be reused after the support platform 202 is properly sterilized. In other implementations, the support platform 202 is manufactured from a plastic and is disposed of after a single use.

The guide tool 102 also includes a pivot assembly 204 that is coupled to the support platform 202. As illustrated the pivot assembly 204 includes a first two-bar linkage 214a and a second two-bar linkage 214b. The pivot assembly 204 is configured to enable the gimbal 206 to rotate substantially along a primary plane of rotation, such that the gimbal 206 pivots about the tip of the catheter 104. For example, the tip of the catheter stays substantially in the same position as the gimbal 206 rotates from a first position to a second position. When pivoting from the first position to the second position, the catheter is substantially maintained within the primary plane of rotation and does not substantially deviate from the primary plane of rotation. In some implementations, the pivot assembly 204 includes a sliding collar about which the gimbal 206 slides to position the gimbal 206 in the bi-stable positions. The bi-stable mechanism of the pivot assembly 204 is described further in relation to FIGS. 3 and 4.

The guide tool 102 also includes a gimbal 206 that is coupled to the pivot assembly 204. In some implementations, the gimbal 206 includes at least one interior ring (or interior gimbal). As illustrated the gimbal 206 includes two interior rings 216a and 216b. Each of the rings of the gimbal 206 are connected together to form, for example, a two-axis gimbal. The rings of the gimbal 206 are connected by flex pivots. The flex pivot may be a substantially friction-free flex bearing. In some implementations, the flex pivots are configured to have substantially no backlash when rotating. In some implementations, the flex pivots provide increasing spring resistance with increasing deviation from a nominal position. In some implementations, the movement of the flex pivots is constrained to limit the movement of the guide axis 218 (and the catheter 104) to between about 0.001° and about 10°, between about 0.001° and about 7°, between about 0.001° and about 3°, between about 0.001° and about 1°, between about 0.001° and about 0.05°, or between about 0.005° and about 0.05° from the primary plane of rotation. The gimbal 206 enables a medical professional to position the tip of the catheter 104 outside of the primary plane of rotation by the above described limited amount. In some implementations, the freedom of movement provided by the gimbal 206 is used by the medical professional to account for patient-to-patient variability in organ size. In other implementations, the gimbal 206 includes a plate, disk, or diaphragm flexure, rather than discrete gimbal rings to enable movement about the guide axis 218. These flexures enable very small linear displacements when compared to the movement enabled by the gimbal rings.

The guide tool 102 also includes a handle 208 that is coupled to the gimbal 206. The guide axis 218 passes through the handle 208 and is the path along which the catheter 104 travels. The interior of the handle 208 includes a catheter advancement mechanism for the advancement and retraction of the catheter 104. For example, the catheter advancement mechanism can include gear reductions that reduce a scale of an input motion such that relatively large input movements by a medical professional result in relatively small advancements of the catheter 104. The gear reductions can include a gearbox, a planetary gearset, a helical/worm gear set, or a combination thereof. In some implementations, a reduction in scale is achieved with a flexural-based structure. For example, the catheter advancement mechanism can include a linkage (e.g., 4 bar, 7 bar, or other type of linkage) that provides an output movement less than a provided input. In some implementations, the catheter advancement mechanism is configured to be substantially backlash free. In some implementations, to advance the catheter 104 by the catheter advancement mechanism, the catheter advancement mechanism includes a circumferential collapsing collet, tangential rollers or wheels, or offset helical rotators that engage with the outside of the catheter 104 via friction. In some implementations, the catheter advancement mechanism is configured to retract the catheter 104 quickly. For example, the guide tool 102 may include a foot pedal that is coupled to the catheter advancement mechanism. When a medical professional activates the foot pedal, the catheter advancement mechanism may quickly retract the catheter 104 from the patient. The medical professional may quickly retract the catheter 104 in instances where the patient begins to move and the patient movement could cause the catheter 104 to cause damage to the eye. In some implementations, the handle 208 (or the catheter advancement mechanism) is enable to retract the catheter 104 at a rate substantially different than the rate of insertion. For example, the rate of extraction may be substantially different because the catheter advancement mechanism is configured to have different rates of scaling for insertion and extraction movements. For example, the insertion scaling may be such that a 0.5 cm motion in the insertion direction by the medical professional results in a 5 µm insertion distance of the catheter 104, while a 0.5 cm motion in the retraction direction by the medical professional results in a 1 cm motion in the retraction direction of the catheter. In some implementations, a retraction movement by the medical professional beyond a predetermined movement results in a controlled, full withdrawal of the catheter 104.

In some implementations, the input motion of the medical professional includes a rotation of the handle 208, which is translated into a linear motion of the catheter 104 by the catheter advancement mechanism. In some implementations, the catheter advancement mechanism is configured to scale a linear or a rotational input movement by a medical professional into a linear movement of the catheter 104. In other implementations, the handle 208 can include a plunger which is depressed to advance the catheter 104. In some implementations, the catheter advancement mechanism or handle 208 includes a linear voltage displacement transducer (LVDT), optical linear encoder, or retro-reflective linear distance sensor to sense the input movement. In some implementations, the handle 208 is rigidly coupled and the input movement is sensed via a touch sensor, such as a capacitive sensor or resistive sensor. The catheter advancement mechanism scales the input motion such that the output motion (or the distance the tip of the catheter 104 travels) is between about between about 1/100 and 1/10000 of the input movement, between about 1/10 and about 1/100 of the input movement, between about 1/10 and about 1/50 of the input movement, or between about 1/10 and about 1/25 of the input movement. For example, the catheter advancement mechanism may translate a 1 cm rotational movement of the handle 208 into a 5 µm linear insertion distance of the catheter 104. The catheter advancement mechanism can have a movement resolution between about 0.01 µm and about 100 µmm.

In some implementations, the scaling performed by the catheter advancement mechanism is rate-based. For example, a relatively small input motion results in a slow catheter insertion rate, and a relatively large input motion results in a faster catheter insertion rate. In other implementations, the catheter advancement mechanism translates an input motion into a predefined linear motion of the catheter 104. For example, the catheter advancement mechanism can include a ratchet mechanism where a rotation to each tooth of the ratchet (or each "click" of the ratchet) advances the catheter a predetermined distance (e.g., between about 1 µm and about 5 µm). Similarly, the handle 208 may include a button that when depressed causes the catheter advancement mechanism to advance the catheter 104 a predetermined or, in some implementations, a variable distance—for example, by actuating a motor to drive the catheter 104.

In some implementations, the catheter advancement mechanism of the handle 208 is powered. For example, the advancement of the catheter 104 can be controlled by the controller 110, which controls an actuator that either directly advances the catheter 104 or acts as an input to the above described catheter advancement mechanism. The actuator may include a piezoelectric actuator, pneumatic actuator, stepper motor, servo, or other electric motor.

In some implementations, the catheter advancement mechanism includes a force sensor. The force sensor is configured to measure the amount of force the catheter 104 is exerting on surrounding tissue as the catheter 104 is advanced by the catheter advancement mechanism into the tissue. In some implementations, if the force measured by the force sensor is above a predetermined threshold, the catheter advancement mechanism may automatically stop and/or retract the catheter 104 so as to not cause a perforation in the tissue.

Still referring to the handle 208 of the guide tool 102, the handle 208 can also be used to position the gimbal 206 (and thus catheter 104) over a target anatomical structure. Use of the handle 208 as a joystick, in combination with the above described inner-rings of the gimbal 206, enables the medical professional to manipulate the position of the catheter tip in relation to the primary plane of rotation. For example, a medical professional can use the handle 208 as a joystick to position the catheter 104 between about 0.001° and about 10° out of plane with the primary plane of rotation.

Figure 3:
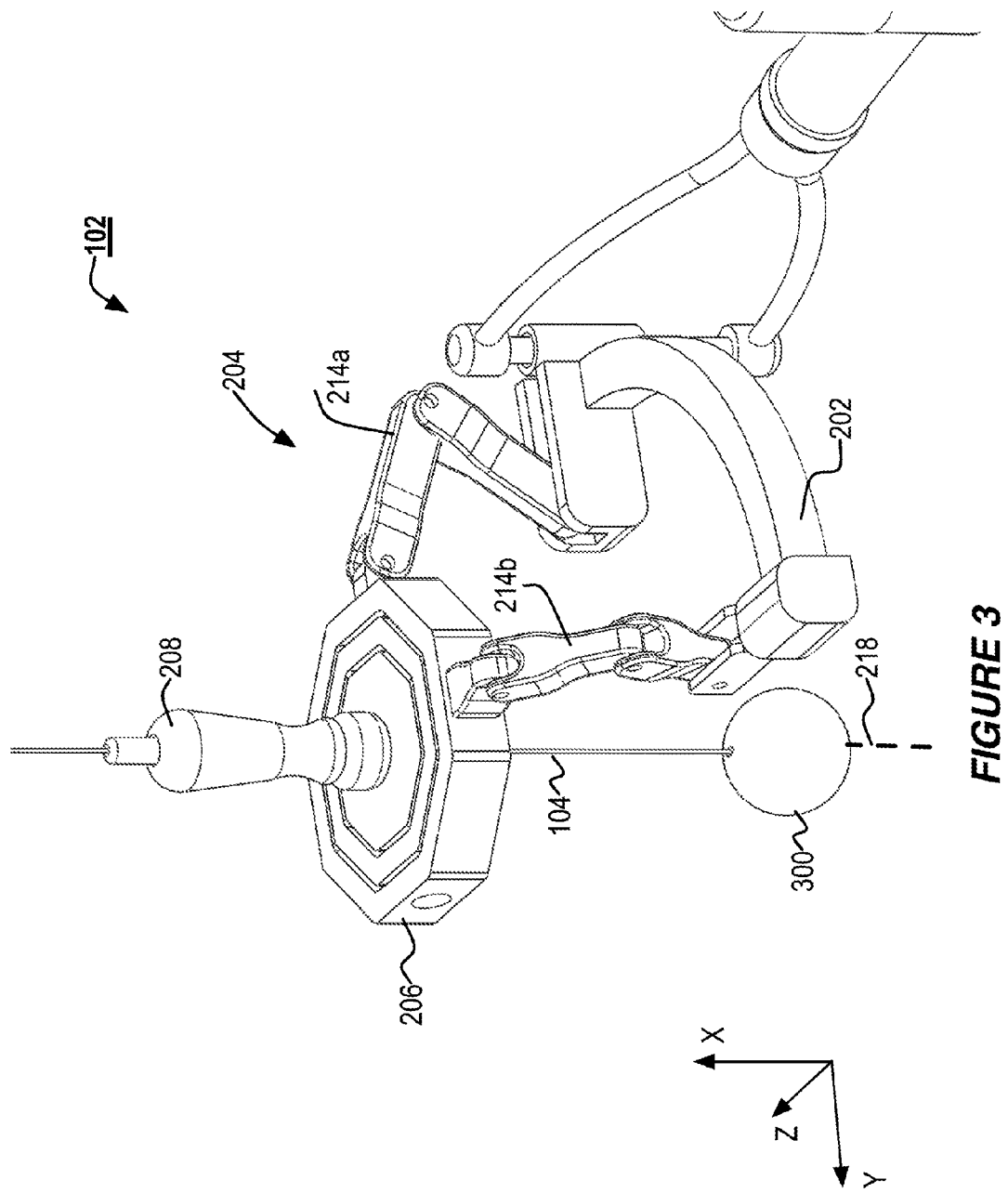
FIG. 3 illustrates a reverse oblique view of the guide tool of FIG. 1 in the first bi-stable position.

FIG. 3 illustrates a reverse oblique view of the guide tool 102. As described above, the guide tool 102 is bi-stable. FIG. 3 illustrates the first position of the bi-stable configuration. In the first position of the bi-stable configuration, the catheter 104 is positioned perpendicular to a target surface. In FIG. 3, the target surface is a surface of a eye 300. The pivot assembly 204 pivots the guide axis 218 (and the catheter 104) from a first position perpendicular to a target surface to a second position tangential to the target surface. The guide axis 218 pivots through a single primary plane of rotation of the gimbal. The primary plane of rotation of the gimbal is the plane defined by the X-axis and Y-axis, as illustrated in FIG. 3. The two-bar linkage 214a lies substantially within the primary plane of rotation as defined by the X-axis and Y-axis and constrains the guide axis 218 to substantially within the primary plane of rotation.

Figure 4:
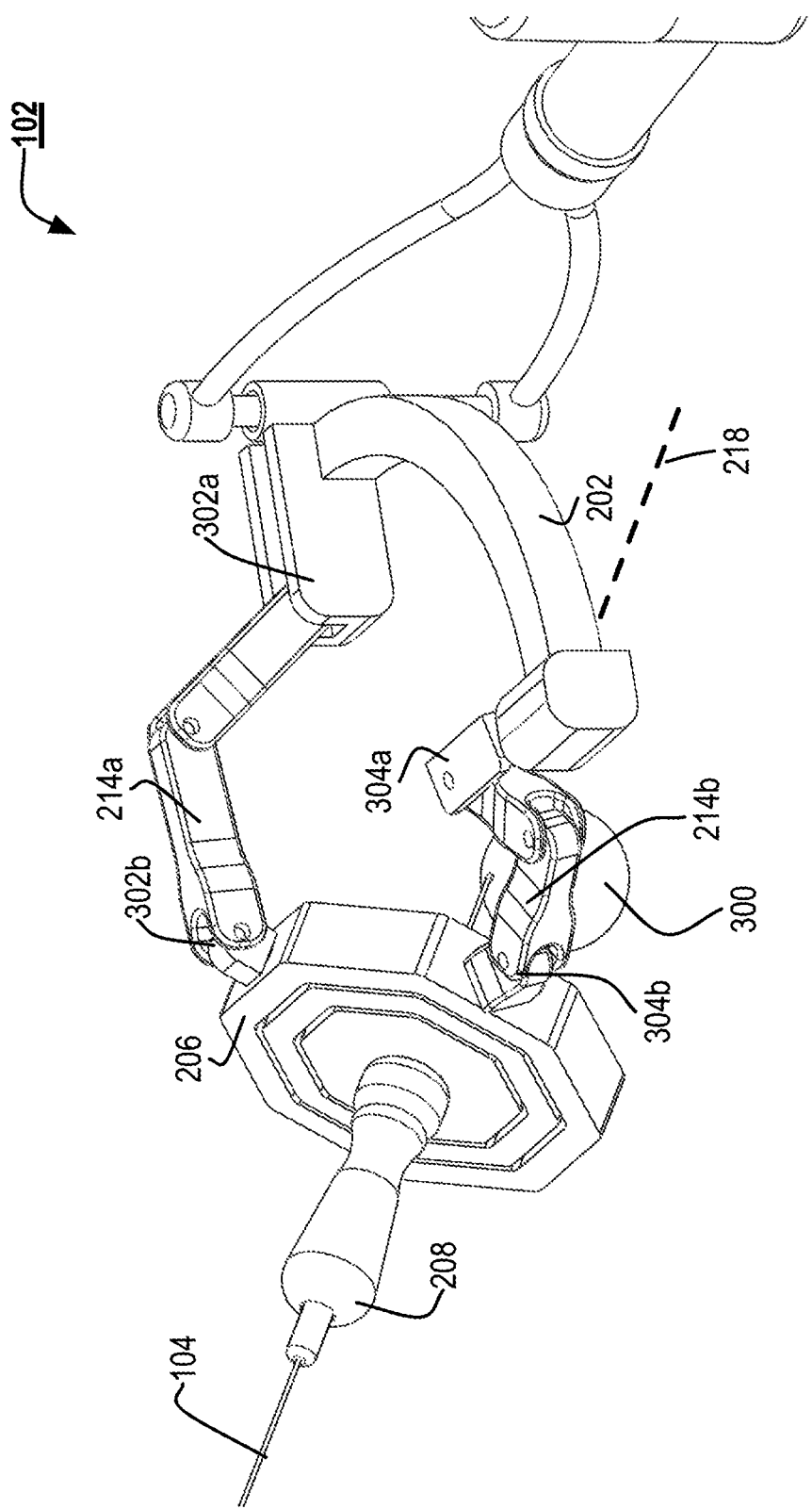
FIG. 4 illustrates a reverse oblique view of the guide tool of FIG. 1 in the second bi-stable position.

FIG. 4 illustrates a reverse oblique view of the guide tool 102 with the guide tool 102 in the second position of the bi-stable configuration. In the second position, the catheter 104 and the guide axis 218 is positioned tangential to the surface of the eye 300. In some implementations, in the second position, the catheter 104 is substantially tangential to the surface of the eye 300. When the catheter 104 is substantially tangential to the surface of the eye 300, the catheter 104 can be between about 0.001° and about 20°, between about 0.001° and about 0.001° and about 10°, between about 0.001° and about 5°, between about 0.001° and about 1°, or between about 0.001° and about 0.05° off the tangent of the surface of the eye 300. The guide tool 102 includes a first set of pivot points 302a and 302b, which couple the first two-bar linkage 214a to the support platform 202 and the gimbal 206, respectively. The guide tool 102 also includes a second set of pivot points 304a and 403b, which couple the second two-bar linkage 214b to the support platform 202 and the gimbal 206, respectively. The first two-bar linkage 214a is placed substantially in the primary plane of rotation of the gimbal (the plane defined by the X axis and Y axis) and maintains the guide axis 218 substantially within the primary plane of rotation as the gimbal 206 pivots. The first two-bar linkage 214a has two stable positions—the retracted position as illustrated in FIG. 3 and the extended position as illustrated in FIG. 4. For example, mechanical restraints may be placed within the pivot points 302a and 302b, which limit the movement of the first two-bar linkage 214a. In some implementations, the medical professional can use the handle 208 or other portion of the guide tool 102 to extend the first two-bar linkage to move the guide tool 102 into the second bi-stable position. In some implementations, the guide tool 102 includes actuators that drive the guide tool 102 between the two bi-stable positions. The actuators can be motors, servos, stepper motors, or pneumatic or hydraulic actuator. The first two-bar linkage 214a can also include dampeners (or dampers) that reduce input vibrations and enable a regulated speed of the transition from the first position to the second position. In some implementations, the dampeners are configured to reduce vibrations caused by the movement between the bi-stable positions and/or vibrations introduced by the medical professional's hand. The dampeners can include rotary dampers, pneumatic dampers, dashpots, or other hydraulic or mechanical damper.

In some implementations, movement between the bi-stable positions is controlled with a controller-released or controller-actuated braking system. For example, the gimbal 206 can be held in place with a braking system that applies a force to a mating surface to hold the pivot assembly 204 (and thus gimbal 206) in the first position. The brake can be released, which allows the medical professional to pivot the gimbal 206 to the second position. The medical professional can either manually apply the braking system to lock the pivot assembly 204 at the second position or the controller 110 can sense when the gimbal 206 is nearing the second position and automatically apply a braking force to stop the gimbal 206 at the second position. The braking force may be applied gradually as to retard the movement of the gimbal 206 and bring the gimbal 206 to a gradual stop at the second position.

As described above, the guide tool 102 also includes a second two-bar linkage 214b. The second two-bar linkage 214b is coupled to the support platform 202 at the pivot point 304a and to the gimbal 206 at the pivot point 304b. The pivot points 304a and 304b are configured to rotate as the gimbal 206 is pivoted to the second bi-stable position. In some implementations, the pivot points 304a and 304b are configured to limit the range of motion of the gimbal 206 to pivot to between the first and second bi-stable positions. For example, the gimbal 206 can include a small protrusion that limits the rotation of the pivot point 304b.

Figure 5:
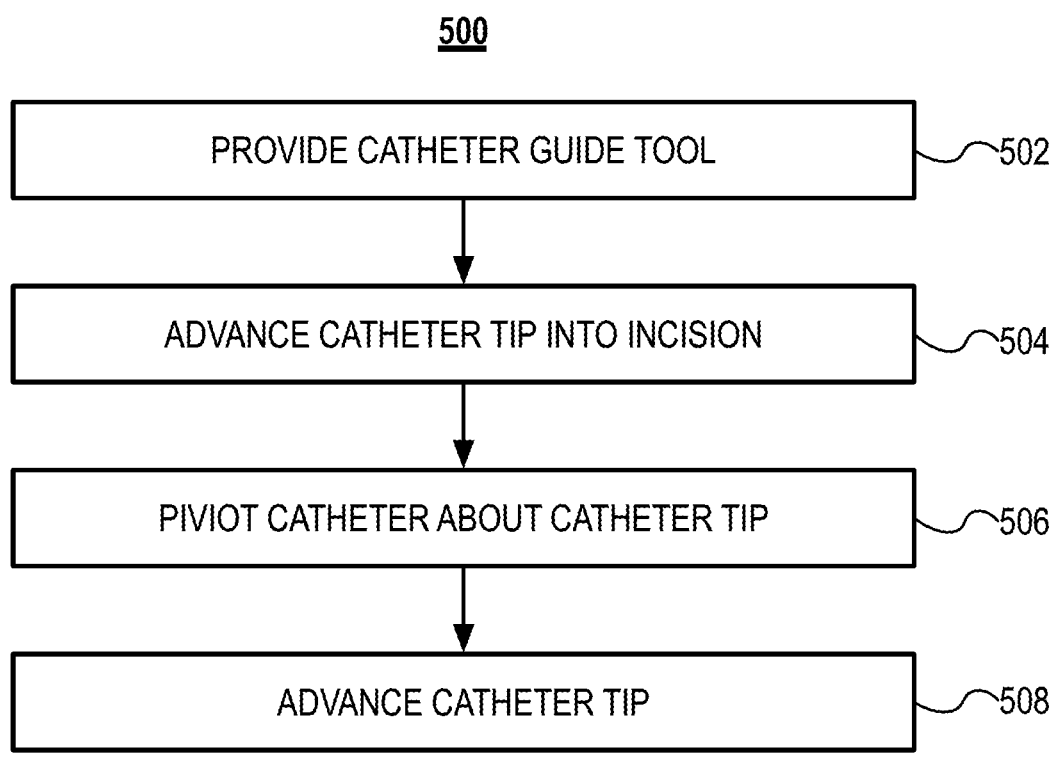
FIG. 5 illustrates an example method for inserting a catheter into an anatomical structure using the system illustrated in FIG. 1.

FIG. 5 illustrates an example method 500 for inserting a catheter into an anatomical structure. The method 500 includes providing a catheter guide tool (step 502). The method 500 also includes advancing a catheter into an incision (step 504). The catheter is pivoted about the catheter tip (step 506) and advanced into the anatomical structure (step 508). In the below example method 500 the anatomical structure is the eye; however, the methods and system described herein could be used with any anatomical structure. For example, the incision could be made in any type of tissue, organ, or organ system, and the target could be a target within or below the tissue, organ, or organ system. As an example, a incision could be made in a patient's scalp and then a portion of the patient's skull could be removed. The target may then be a location within the patient's brain.

As set forth above, the example method 500 includes providing a catheter guide tool (step 502). The guide tool is the guide tool described above in relation to FIGS. 1-4. As an overview, the guide tool includes a gimbal that includes a guide axis along which a catheter is advanced and retracted. The guide tool includes a pivot assembly that couples the gimbal to a support platform. The pivot assembly enables the gimbal to pivot the guide axis and the catheter from a first position to a second position. Throughout the transition from the first position to the second position, the catheter remains substantially in a primary plane of rotation. In some implementations, the guide tool is bi-stable between the first and the second position.

After an incision is made in the target surface of the eye, the tip of the catheter is advanced into the incision (step 504). For the example method 500 where the catheter is inserted into the eye, the incision is made in the sclera of the eye. In some implementations, after the incision in the target surface of the eye, the tip of the catheter is positioned into the incision using the guide tool provided in step 502 of the method 500. In some implementations, when inserting the catheter into the incision, the catheter is inserted between two layers of tissue in the eye. For example, the tip of the catheter is inserted just between the choroid and the retina.

The catheter is then pivoted about the tip of the catheter using the guide tool (step 506). As described above, the guide tool is bi-stable. When pivoted, the guide tool moves from the first bi-stable position where the catheter is perpendicular to the target surface of the eye to the second bi-stable position, which moves the catheter tangential to the target surface of the eye. When the catheter is moved tangential to the target surface of the eye, the tip of the catheter is maintained between the two layers of tissue that the tip of the catheter was inserted in step 506.

Once in the tangential position, the catheter is advanced (step 508). For example, when the tip of the catheter is inserted between the choroid and the retina the tip of the catheter is advanced toward the posterior of the eye. The catheter is advanced by the guide tool. For example, a medical profession provides a input movement to the guide tool, such as a rotation of the handle, which is translated by the catheter advancement mechanism into a linear movement of the catheter. The catheter advancement mechanism can include a gear reduction that reduces a scale of the input motion such that relatively large input movements by the medical professional result in relatively small advancements of the catheter.

In some implementations, once the catheter reaches the target location, a fluid can be passed or withdrawn through catheter. For example, sodium hyaluronate or a therapeutic agent can be delivered to the target location through the catheter. In some implementations, a dilatory liquid can be passed through the catheter as the catheter is advanced toward the target location. The dilatory liquid can be used to separate tissue layers prior to the advancement of the catheter.

The invention may be embodied in other specific forms without departing from the spirit or essential characteristics thereof. The forgoing implementations are therefore to be considered in all respects illustrative, rather than limiting of the invention.

What is claimed:

1. A catheter guide tool comprising:
   a gimbal comprising a guide axis;
   a catheter advancement mechanism coupled to the gimbal and configured to advance a catheter along the guide axis; and
   a pivot assembly comprising:
      a first two-bar linkage coupling the gimbal to a support platform and positioned substantially within a single primary plane of rotation of the gimbal; and
      a second two-bar linkage coupling the gimbal to the support platform and positioned substantially perpendicular to the single primary plane of rotation of the gimbal, the pivot assembly configured to pivot the guide axis from a first position perpendicular to a target surface to a second position substantially tangential to the target surface along the single primary plane of rotation of the gimbal.

2. The catheter guide tool of claim 1, wherein the second two-bar linkage is coupled to the gimbal by a first rotational joint and to the support platform by a second rotational joint.

3. The catheter guide tool of claim 1, wherein the pivot assembly is bi-stable between the first position and the second position.

4. The catheter guide tool of claim 1, wherein the gimbal further comprises at least one interior gimbal to provide limited movement to within about 0.001° and about 10° of the primary plane of rotation.

5. The catheter guide tool of claim 1, wherein the catheter advancement mechanism is configured to scale an output movement to between about 1/10 and about 1/10000 of an input movement.

6. The catheter guide tool of claim 1, wherein the catheter advancement mechanism has a movement resolution between about 0.1 μm and about 100 μm.

7. The catheter guide tool of claim 1, further comprising an actuator to drive the pivot assembly from the first position to the second position.

8. The catheter guide tool of claim 1, wherein the catheter advancement mechanism further comprises at least one force sensor.

9. The catheter guide tool of claim 1, wherein the support platform further comprises an articulating arm.

10. The catheter guide tool of claim 1, wherein the pivot assembly further comprises a damper.

11. A method for inserting a catheter, the method comprising:
   providing a catheter guide tool comprising:
      a gimbal comprising a guide axis;
      a catheter advancement mechanism coupled to the gimbal and configured to advance a catheter along the guide axis; and
      a pivot assembly comprising:
         a first two-bar linkage coupling the gimbal to a support platform and positioned substantially within a single primary plane of rotation of the gimbal; and
         a second two-bar linkage coupling the gimbal to the support platform and positioned substantially perpendicular to the single primary plane or rotation of the gimbal, the pivot assembly configured to pivot the guide axis from a first position perpendicular to a target surface to a second position substantially tangential to the target surface along a single primary plane of rotation of the gimbal;
   advancing a catheter tip into an incision of an organ;
   pivoting the gimbal to the second position about the catheter tip; and
   advancing the catheter tip toward an anatomical target within the organ.

12. The method of claim 11, wherein the incision is made in a sclera of an eye.

13. The method of claim 12, further comprising advancing the tip of the catheter toward the posterior of the eye.

14. The method of claim 11, further comprising injecting a fluid through the catheter tip.

15. The method of claim 11, wherein the linkage is bi-stable between the first position and the second position.

16. The method of claim 11, further comprising scaling an output movement by the catheter guide tool to between about 1/10 and about 1/10000 of an input movement to the catheter guide tool.

17. The method of claim 11, further comprising pivoting the gimbal to the second position with an actuator.

18. The method of claim 11, further comprising damping the pivoting of the gimbal to the second position with a damper.

* * * * *